(12) United States Patent
Duc et al.

(10) Patent No.: US 10,595,977 B2
(45) Date of Patent: Mar. 24, 2020

(54) THREAD INSERTION DEVICES (71) Applicant: Allergan Industrie SAS, Pringy (FR)

(72) Inventors: Antoine Duc, Saint Jean le Vieux (FR); Bastien Mandaroux, Metz-Tessy (FR)

(73) Assignee: Allergan Industrie, SAS, Pringy (FR)

( * ) Notice: Subject to any disclaimer, the term of this patent is extended or adjusted under 35 U.S.C. 154(b) by 53 days.

(21) Appl. No.: 15/414,195

(22) Filed: Jan. 24, 2017

(65) Prior Publication Data
US 2018/0206963 A1    Jul. 26, 2018

(51) Int. Cl.
*A61F 2/02* (2006.01)
*A61F 2/00* (2006.01)
*A61F 2/10* (2006.01)

(52) U.S. Cl.
CPC ............ *A61F 2/0059* (2013.01); *A61F 2/105* (2013.01); *A61F 2/02* (2013.01)

(58) Field of Classification Search
CPC .......... A61F 2/0059; A61F 2/105; A61F 2/10; A61B 17/3468; A61B 17/0482; A61B 17/06; A61B 17/06004; A61B 2017/06009; A61B 2017/06014; A61B 2017/06019; A61B 2017/06023; A61B 2017/06028; A61B 2017/06042; A61B 2017/06047; A61B 2017/06052

See application file for complete search history.

(56) References Cited

U.S. PATENT DOCUMENTS

| | | | |
|---|---|---|---|
| 1,250,114 A | 12/1917 | Bigelow et al. | |
| 1,558,037 A | 10/1925 | Morton | |
| 1,591,021 A | 7/1926 | Davis | |
| 2,092,427 A * | 9/1937 | Ross | A61F 13/2051 604/364 |
| 2,302,986 A | 11/1942 | Vollrath | |
| 2,571,653 A | 10/1951 | Victor | |

(Continued)

FOREIGN PATENT DOCUMENTS

| | | |
|---|---|---|
| EP | 0648474 A1 | 4/1995 |
| EP | 0809968 A1 | 12/1997 |

(Continued)

OTHER PUBLICATIONS

Bleyer, Mark, SIS Facial Implant 510(k) Summary, Cook Biotech, Inc., May 19, 2005.

*Primary Examiner* — Suba Ganesan
*Assistant Examiner* — Aren Patel
(74) *Attorney, Agent, or Firm* — Nathan S. Smith; Danny Mansour; Morgan, Lewis & Bockius LLP (57) ABSTRACT

Devices and methods for inserting an implant into skin or other tissue of a patient can include an insertion device that can enclose and support a hyaluronic thread as it is injected into a patient's skin or other tissue. The device can include a cover member, a non-tubular support member, and the thread. The cover member can have a proximal portion, a closed distal portion, and an inner cavity extending from the proximal portion toward the closed distal portion. The thread can be positioned along a longitudinal length of support member, between the support member and the cover member. The non-tubular support member can extend within the inner cavity of the cover member. The cover member can be moveable relative to the support member to expose the thread.

22 Claims, 5 Drawing Sheets

(56) References Cited

U.S. PATENT DOCUMENTS

| | | | | |
|---|---|---|---|---|
| 3,204,635 | A * | 9/1965 | Voss | A61F 13/26 604/14 |
| 3,674,026 | A * | 7/1972 | Werner | A61F 13/26 604/14 |
| 3,910,282 | A | 10/1975 | Messer et al. | |
| 4,402,308 | A * | 9/1983 | Scott | A61M 5/31511 604/218 |
| 4,451,253 | A * | 5/1984 | Harman | A61B 17/3468 600/7 |
| 4,820,267 | A * | 4/1989 | Harman | A61K 9/0024 604/60 |
| 4,846,886 | A | 7/1989 | Fey et al. | |
| 4,957,744 | A | 9/1990 | della Valle et al. | |
| 4,994,028 | A * | 2/1991 | Leonard | A61M 37/0069 604/60 |
| 5,116,358 | A | 5/1992 | Granger et al. | |
| 5,211,644 | A | 5/1993 | VanBeek et al. | |
| 5,215,535 | A | 6/1993 | Gettig | |
| 5,254,105 | A * | 10/1993 | Haaga | A61B 10/0233 604/265 |
| 5,258,013 | A | 11/1993 | Granger et al. | |
| 5,304,119 | A * | 4/1994 | Balaban | A61M 37/0069 604/59 |
| 5,350,385 | A | 9/1994 | Christy | |
| 5,366,447 | A * | 11/1994 | Gurley | A61M 37/0069 604/107 |
| 5,478,327 | A | 12/1995 | McGregor et al. | |
| 5,599,293 | A * | 2/1997 | Orenga | A61F 13/2085 604/11 |
| 5,735,827 | A * | 4/1998 | Adwers | A61M 5/3213 604/192 |
| 5,752,970 | A | 5/1998 | Yoon | |
| 5,824,335 | A | 10/1998 | Dorigatti et al. | |
| 5,997,513 | A | 12/1999 | Smith | |
| 6,102,920 | A | 8/2000 | Sullivan | |
| 6,159,233 | A | 12/2000 | Matsuzawa | |
| 6,162,203 | A * | 12/2000 | Haaga | A61B 10/0275 128/898 |
| 6,214,030 | B1 | 4/2001 | Matsutani et al. | |
| 6,450,937 | B1 * | 9/2002 | Mercereau | A61F 2/00 128/898 |
| 6,547,762 | B1 | 4/2003 | Botich | |
| 6,936,297 | B2 | 8/2005 | Roby et al. | |
| 7,041,088 | B2 | 5/2006 | Nawrocki et al. | |
| 7,504,386 | B2 | 3/2009 | Pressato et al. | |
| 7,559,952 | B2 | 7/2009 | Pinchuk | |
| 7,666,339 | B2 | 2/2010 | Chaouk et al. | |
| 7,722,582 | B2 | 5/2010 | Lina et al. | |
| 7,998,170 | B2 | 8/2011 | Cunningham | |
| 8,177,792 | B2 * | 5/2012 | Lubock | A61M 37/0069 600/431 |
| 8,652,216 | B2 | 2/2014 | Chen | |
| 9,801,688 | B2 * | 10/2017 | Jones | A61B 90/39 |
| 2001/0008937 | A1 | 7/2001 | Callegaro et al. | |
| 2001/0050084 | A1 * | 12/2001 | Knudson | A61M 5/3271 604/192 |
| 2002/0026039 | A1 | 2/2002 | Bellini et al. | |
| 2003/0023250 | A1 | 1/2003 | Watschke | |
| 2003/0097079 | A1 * | 5/2003 | Garcia | A61M 37/0069 600/7 |
| 2003/0109769 | A1 * | 6/2003 | Lowery | A61M 37/0069 600/7 |
| 2004/0192643 | A1 | 9/2004 | Pressato et al. | |
| 2005/0033362 | A1 | 2/2005 | Grafton | |
| 2005/0075606 | A1 | 4/2005 | Botich | |
| 2005/0182446 | A1 | 8/2005 | DeSantis | |
| 2006/0041320 | A1 | 2/2006 | Matsuda | |
| 2006/0136070 | A1 | 6/2006 | Pinchuk | |
| 2008/0119876 | A1 | 5/2008 | Price et al. | |
| 2008/0125766 | A1 * | 5/2008 | Lubock | A61B 17/3468 606/33 |
| 2008/0139928 | A1 * | 6/2008 | Lubock | A61B 10/0275 600/567 |
| 2008/0167674 | A1 | 7/2008 | Bodduluri et al. | |
| 2009/0131908 | A1 * | 5/2009 | McKay | A61B 17/3468 600/414 |
| 2009/0209804 | A1 * | 8/2009 | Seiler | A61B 17/3468 604/511 |
| 2009/0318875 | A1 * | 12/2009 | Friedman | A61B 17/3468 604/187 |
| 2010/0256596 | A1 | 10/2010 | Chomas | |
| 2011/0093088 | A1 | 4/2011 | Chen | |
| 2011/0152926 | A1 | 6/2011 | Vetrecin | |
| 2011/0263724 | A1 | 10/2011 | Gurtner et al. | |
| 2011/0282447 | A1 * | 11/2011 | Niu | A61B 17/06 623/13.11 |
| 2012/0108895 | A1 | 5/2012 | Neuman | |
| 2012/0215230 | A1 | 8/2012 | Lubock et al. | |
| 2012/0245629 | A1 | 9/2012 | Gross et al. | |
| 2013/0122068 | A1 | 5/2013 | Fermanian et al. | |
| 2013/0211374 | A1 | 8/2013 | Hetherington | |
| 2013/0226235 | A1 | 8/2013 | Fermanian et al. | |
| 2013/0274222 | A1 | 10/2013 | Horne et al. | |
| 2013/0310750 | A1 | 11/2013 | Hopman | |
| 2014/0221940 | A1 | 8/2014 | Clauson et al. | |
| 2014/0228971 | A1 | 8/2014 | Kim | |
| 2015/0209265 | A1 | 7/2015 | Horne | |
| 2015/0209523 | A1 | 7/2015 | Horne et al. | |
| 2015/0327972 | A1 | 11/2015 | Horne et al. | |
| 2016/0007990 | A1 | 1/2016 | Solish et al. | |
| 2016/0074307 | A1 | 3/2016 | Gurmer et al. | |
| 2016/0213813 | A1 | 7/2016 | Gunner et al. | |
| 2017/0049972 | A1 | 2/2017 | Persons | |
| 2017/0156754 | A1 * | 6/2017 | Valbuena | A61B 17/3468 |
| 2017/0290987 | A1 | 10/2017 | Mandaroux et al. | |
| 2018/0206964 | A1 | 7/2018 | Duc et al. | |
| 2018/0206965 | A1 | 7/2018 | Duc et al. | |
| 2018/0206966 | A1 | 7/2018 | Duc et al. | |
| 2018/0206967 | A1 | 7/2018 | Duc et al. | |

FOREIGN PATENT DOCUMENTS

| | | |
|---|---|---|
| EP | 2422832 | 2/2012 |
| EP | 2422832 A2 | 2/2012 |
| EP | 2103262 B1 | 2/2013 |
| EP | 2184016 | 4/2013 |
| EP | 2671516 | 12/2013 |
| GB | 2336783 | 5/2003 |
| KR | 20120007473 | 1/2012 |
| KR | 101246570 | 3/2013 |
| KR | 20130036921 | 4/2013 |
| KR | 20130130436 | 12/2013 |
| KR | 20130132196 | 12/2013 |
| KR | 20140029007 | 3/2014 |
| WO | 199001349 A1 | 2/1990 |
| WO | 1992013579 A1 | 8/1992 |
| WO | 200100190 A2 | 1/2001 |
| WO | 2004022603 A1 | 3/2004 |
| WO | 2006065837 A2 | 6/2006 |
| WO | 2010028025 A1 | 3/2010 |
| WO | 2011109129 A1 | 9/2011 |
| WO | 2011109130 A1 | 9/2011 |
| WO | 2012054301 A1 | 4/2012 |
| WO | 2012054311 A1 | 4/2012 |
| WO | 2013055832 A1 | 4/2013 |
| WO | 2013082112 A1 | 6/2013 |
| WO | WO 2012/174464 | 5/2014 |
| WO | WO2015105269 A1 | 7/2015 |

* cited by examiner

THREAD INSERTION DEVICES

BACKGROUND

Field of the Inventions

The present disclosure relates generally to systems and methods for insertion of an implant, and more particularly, to insertion devices that can enclose and support an implant, such as a hyaluronic thread, as it is injected into a patient's skin or other tissue.

Background

In recent years, millions of men and women have elected to receive dermal filler injections to rejuvenate aging skin and look younger without surgery or significant downtime. A dermal filler injection is a procedure through which a gel-like, volumizing, substance is injected subcutaneously to restore lost volume, add volume to facial features and contours, or smooth fine lines and creases.

Some dermal filler injections are performed using a thread or other implant. Once inserted, the threads used for dermal filler injections can hydrate and expand or swell within the skin of a patient, thereby lessening the appearance of wrinkles, folds, and/or sagging portions of skin.

To insert a thread into the patient, conventional suture procedures can be implemented. For example, using a conventional procedure, a physician couples a thread to a needle and inserts the needle through the skin until achieving a desired placement, which may be adjacent to or under a wrinkle. With the thread placed along or underneath the wrinkle, the needle can be removed and as the thread hydrates, the wrinkle can be "filled" and become less prominent, thus smoothing the skin and achieving a desired aesthetic for the patient.

SUMMARY

The present application discloses various improvements for thread insertion devices and related procedures that can be used to treat humans and/or animals. The devices and procedures can be used, for example, in the context of dermal fillers, surgery (e.g., placing sutures), drug delivery, negative pressure wound therapy, and wound dressing.

In plastic surgery, hyaluronic acid is a common substance used for wrinkle filling. Although hyaluronic acid is typically used as a gel that is injected as a wrinkle filler, some embodiments disclosed herein can utilize hyaluronic acid in a solid form as an implant, e.g., as a hyaluronic acid thread ("HA thread" or "thread").

However, in accordance with some embodiments disclosed herein in the realization that because HA threads are hydrophilic, the mechanical integrity of the thread can rapidly degrade during an implantation procedure. Thread failure can result in improper placement or other complications during the procedure. Thus, a thread that is exposed during insertion of the thread into a patient can become hydrated, causing the thread to swell or expand prematurely and/or lose its tensile strength. If the thread swells within a needle or insertion device, the thread will become lodged within the needle and unable to move relative to the insertion device. The thread can therefore block the needle lumen, prevent separation of the thread from the insertion device, or otherwise complicate the thread placement procedure. In some instances, the swelling of a thread may cause it to engage with skin tissue before the thread has reached a desired position subcutaneously. Thus, the thread becomes immovable during insertion of the thread into the patient. Further, during insertion, friction between the thread and the tissue may increase beyond a tensile strength of the thread and cause the thread to break and separate from the insertion device.

Further, some embodiments of the present devices and methods also contrast with various conventional thread placement devices that include a needle tip that engages a thread at its midsection and allows the thread to fold backwardly or proximally along a length of the needle. In accordance with some embodiments disclosed herein in the realization that because the thread is divided into two strands that extend along the length of the needle, the injection also results in a double-stranded thread placement in which the two strands will swell in situ. Although this may be acceptable in some applications, these conventional devices and procedures are limited because they have a "minimum expansion size" of twice that of a single thread. Accordingly, some of the embodiments disclosed herein enable a single strand of thread to be placed along a desired position instead of the conventional double-stranded thread placement. Advantageously then, some embodiments allow for a lower "minimum expansion size" that can allow a physician to treat wrinkles that are not otherwise good candidates for treatment using only the conventional devices or methods.

Further, because some embodiments disclosed herein "push" a distal end of the thread through the skin, the physician need only to make a single piercing instead of entry and exit piercings required by conventional devices and methods that use a needle whose proximal end attaches to a distal end of the thread and pulls the thread through the entry and exit piercings.

Therefore, some embodiments of the thread insertion devices and procedures disclosed herein can advantageously minimize the number of piercings through the skin, reduce the risk of thread contamination during the insertion procedure, and/or minimize pain and bruising to the patient. Further, some embodiments of the thread insertion devices and procedures disclosed herein can advantageously avoid breakage of the thread during insertion, facilitate safer and easier insertion of the thread, and/or permit greater control over the thread length and insertion depth.

Although particular embodiments of the present disclosure may be disclosed in the context of an implant comprising a thread, it is contemplated that embodiments can be used with various implants. For example, embodiments can be used with an implant comprising a thread, a series of hinged members, or a tube. Further, embodiments can comprise an implant comprising a rigid material, a flexible material, HA threads material, and a material comprising a state of matter including solid, liquid, or any state there between. The implant can comprise a medication and/or medical fluid that are configured to be released by the implant.

In some embodiments, the thread insertion device can comprise a cover member configured to protect an implant, or portions of a device that will be inserted into a patient. The cover member can prevent contamination or damage to a thread. The cover member can also maintain a shape or alignment of a thread relative to a thread insertion device.

The cover member can comprise a cavity or passage configured for a thread to be positioned therein. For example, the cover member can retain at least a portion or an entirety of the thread within a cavity or passage. Contamination or damage to the thread can be prevented when the thread is positioned within a cavity or passage of the cover member. The cover member can prevent contamination of the thread from exposure to an ambient environment, or from a person touching the thread. Further, damage to the thread can be avoided by preventing inadvertent touching or engagement of the thread. Damage to the thread can also be avoided by preventing exposure of the thread to moisture from the patient's skin or tissue, e.g., dermis, epidermis, and subcutaneous tissue, during insertion of the thread.

In some embodiments, the cover member can permit a thread to be positioned along an outer surface of the cover member. The cover member can permit a thread to be positioned along an inner surface of the cover member. The cover member can also provide support to maintain alignment of the thread during insertion.

In some embodiments, the thread can be retained and/or engaged with the cover member and/or a portion of the thread insertion device. Further, the cover member and/or a portion of the thread insertion device can be used to move a thread relative to the insertion device or separate a thread from the insertion device.

For example, the insertion device can comprise one or more portions that extend along an outer surface and/or within the cover member. The thread insertion device can comprise a moveable member within the cover member. A piston can be positioned within a cavity of the cover member. The piston can cause movement of the thread supported on or coupled with the insertion device. Movement of a portion of the insertion device, e.g., the cover member and/or the piston, can release or separate a thread from the insertion device.

In some embodiments, the thread insertion device can comprise a cover member that can be engaged against a thread to retain the thread with the insertion device. A portion of the cover member can be crimped, or compressed, or adhered to engage a portion of a thread. The thread can be adhered to the cover member. To release a thread from the insertion device, a portion of the cover member engaged against a thread can be moved or expanded, or the thread can be separated from the portion of the cover member.

The cover member can comprise a flexible or rigid body. The body can comprise a cross-sectional profile that defines a cavity. A shape of a cross-sectional profile of the cover member can comprise an open perimeter, a closed perimeter, a circle, a square, a rectangle, an L-shape, and/or a U-shape. The cover member can comprise an inner surface cross-sectional profile having portions that are tubular along a length of the cover member.

A portion of the cover member can comprise an opening, e.g., a channel or an aperture, between an inner cavity and an outer surface of the cover member. The cover member can permit a thread to be moved through the opening. A thread can be coupled to the insertion device by a portion of the thread that extends through the opening.

The cover member can comprise a proximal portion and a distal portion. The proximal portion can comprise an opening into a cavity of the cover member. The proximal portion can be coupled to other portions of the thread insertion device. The proximal portion can be releasably coupled to a portion of the insertion device.

A cavity of the cover member can extend toward the distal portion of the cover member. The cavity can extend toward a closed distal portion of the cover member. The distal portion of the cover member can comprise a tip portion. The tip portion can comprise an outer surface that tapers toward a point. A tapered or pointed tip can permit the cover member to pierce the patient's skin or tissue to allow insertion of the cover member and thread. The tip can comprise a point, a bevel, or a multiple-sided cutting point, e.g., a pin, a needle, or a trocar. The tip portion can comprises an outer surface that is rounded or blunt. A round or blunt tip can permit insertion of the cover member through an opening of a patient without piercing or causing damage to the patient.

The cover member can comprise a rigid material, a flexible material, a membrane, and/or a heat-shrinkable sleeve. A portion of the cover member comprising a flexible material can extend along an outer surface of the thread. The thread can be positioned between a portion of the cover member comprising a rigid material, and a portion of the cover member comprising a flexible material. The flexible material can enclose a thread during insertion, and can be separated from the thread to permit release of the thread.

The insertion device can separate or move a cover member away from a thread, or move a thread away from a cover member. A cover member can be moved to uncover or expose a thread. The insertion device can tear a portion of a cover member. The insertion device can tear a flexible portion of the cover material to expose a thread. The cover member can comprise a dissolvable material that degrades or separates from a thread. The dissolvable material of the cover member can break down or change phase when exposed to a temperature. The dissolvable material can dissolve when exposed to a patient's body temperature.

The cover member can comprise a shape memory material configured to move to expose or release a thread. The cover member can enclose or retain a thread within a portion comprising a shape memory material, and move to expose or release a thread. The shape memory material can be activated or deactivated by heating the cover member. The cover member can be heated by applying electricity to the cover member, e.g., resistive heating, or exposing the cover member to the patient's body heat during insertion of the device into the patient.

A support member of the thread insertion device can maintain alignment of a thread relative to the insertion device and permit positioning of the thread within a patient. A portion of a thread can extend along the support member. The support member and a thread adjacent to the support member can move together. The support member can cover or surround a thread to prevent exposure of the thread to contamination or potential damage.

A thread can be engaged against the support member to permit movement of the thread with the insertion device. A thread can be positioned between the support member and a cover member. A flexible cover member can extend around the support member to retain a thread between a support member and the flexible cover member. The thread can be adhered to the support member, e.g., glued, taped, or engaged by a portion of the support member, e.g., compressed or crimped.

The support member can comprise a shaft, a rod, and/or a plate having a longitudinal length, and/or can comprise a proximal portion and a distal portion. The proximal portion of the support member can be coupled with other portions of the thread insertion device. The proximal portion of the support member can be releasably coupled with a portion of the insertion device. The insertion device can permit a releasably coupled support member to be separated from the insertion device.

The distal portion of a support member can comprise a tip portion. The tip portion can comprise an outer surface that tapers toward a point. A tapered or pointed tip can permit the support member to pierce a patient's skin or tissue and allow insertion of a portion of the insertion device and thread. The tip can comprise a point, a bevel, or a multiple-sided cutting point, e.g., a pin, a needle, or a trocar. The tip portion can comprise an outer surface that is rounded or blunt. A round or blunt tip can permit insertion of the support member through an opening of a patient without piercing or causing damage to the patient. A distal portion of the support member can be engaged against a cover member to tear the cover member and permit release of a thread from the insertion device.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the present disclosure are described below with reference to the drawings. The illustrated embodiments are intended to illustrate, but not to limit, the present disclosure. The drawings contain the following figures.

DETAILED DESCRIPTION

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Further, while the present description sets forth specific details of various embodiments, it will be appreciated that the description is illustrative only and should not be construed in any way as limiting. Additionally, it is contemplated that although particular embodiments of the present disclosure may be disclosed or shown in the context of HA thread insertion devices, such embodiments can be used with various devices and implants. Furthermore, various applications of such embodiments and modifications thereto, which may occur to those who are skilled in the art, are also encompassed by the general concepts described herein.

The present application addresses several operational challenges encountered in prior HA thread insertion devices and related procedures. This application provides numerous improvements that enable the physician to control the device more easily, thereby allowing precise positioning of the implant while minimizing trauma to the patient.

For example, in accordance with some embodiments, the present application discloses various features and advantages of thread insertion devices and procedures that can be used to deliver an implant into skin or other tissue of a patient. The thread insertion device can avoid contamination a HA thread and protect the thread's mechanical properties during insertion. The thread insertion device can also permit a physician to precisely position the implant while minimizing trauma to the patient. The present disclosure, along with co-pending U.S. patent application Ser. No. 15/414,248, Ser. No. 15/414,278, Ser. No. 15/414,219, and Ser. No. 15/414,306, each filed on the same day as the present application, includes various features that can be interchangeably implemented into embodiments of thread insertion devices and methods of their use and the contents of these applications are incorporated herein in by reference in their entireties. For example, various aspects of the engagement mechanisms, actuation components, cover members, handles, and other features for delivering, protecting, engaging, advancing, or otherwise handling a needle and/or thread, can be combined or substituted with features of embodiments disclosed herein.

Further, some embodiments of the thread insertion devices and procedures disclosed herein can advantageously allow a single strand of HA thread to be positioned in situ as opposed to conventional double-stranded thread placement. Some embodiments disclosed herein relate to enclosure-type thread insertion devices.

Figure 1:
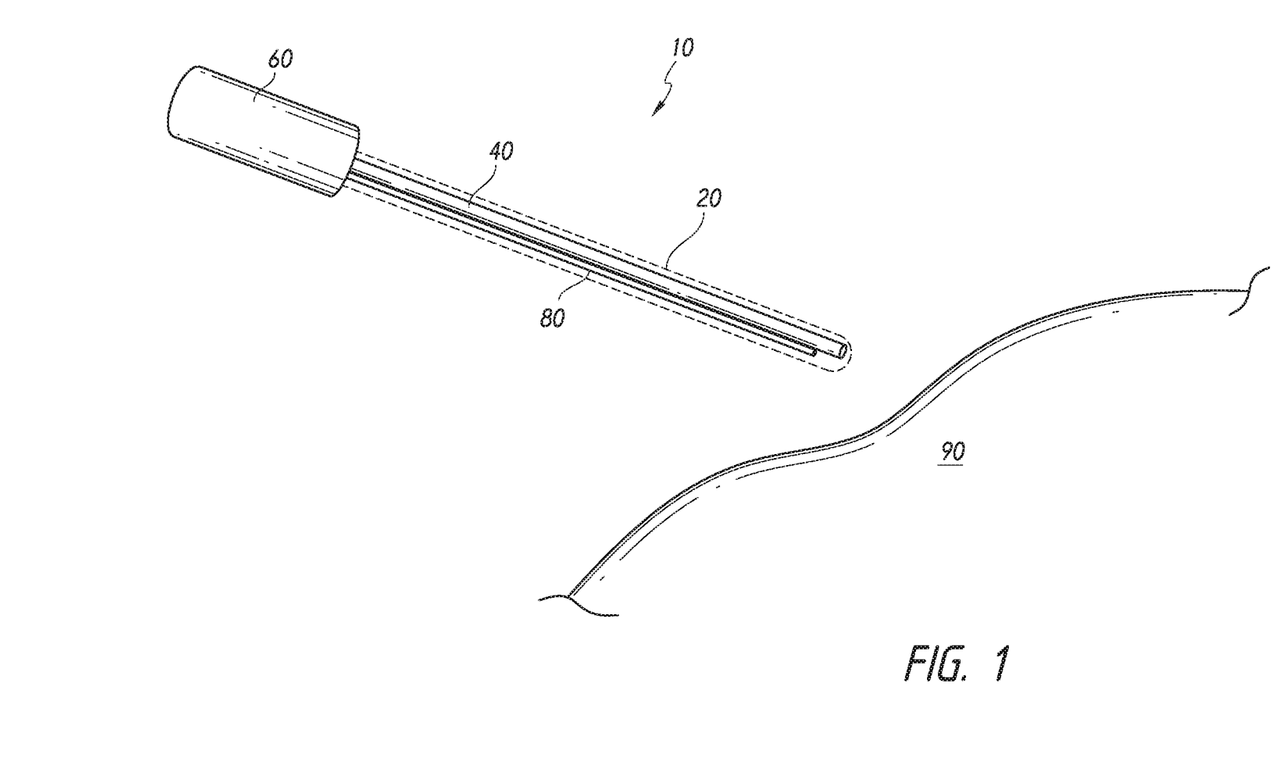
FIG. 1 is a front view of an insertion device, according to some embodiments.

Referring to the figures, a schematic illustration of a general embodiment of a thread insertion device 10 is shown in FIG. 1. The insertion device 10 can comprise a cover member 20, a support member 40, and a base 60. A HA thread 80 can be positioned between the cover member 20 and the support member 40 (each of the embodiments discussed herein refers to the HA thread 80, but the HA thread 80 can be substituted, modified, or replaced in any of the embodiments with a thread or suture having a different type, length, and/or size).

The insertion device 10 comprises a proximal portion and a distal portion. The proximal portion comprises the base 60, and the distal portion comprises the cover member 20 and the support member 40. The base 60 can comprise one or more portions. The base 60 can comprise a first portion and a second portion that is movable relative to the first base portion. The base 60 can comprise a movable member, e.g., a button or engagement member, to permit a portion of the insertion device to be separated from the base 60.

The support member 40 can be coupled to the base 60 and extend from the base 60 toward the distal portion of the insertion device 10. The support member 40 can comprise a shaft, a rod, and/or a plate having a longitudinal length. A cross-section, transverse to the longitudinal length of the support member 40, can be non-tubular and/or tubular, and can comprise a shape or profile such as a circle, a square, a rectangle, an L-shape, and/or a U-shape.

The cover member 20, illustrated in broken lines, can extend around the outer surface of the support member 40. The cover member 20 can be coupled to the base 60. The cover member 20 can comprise a rigid material, a flexible material, or any combination thereof. In some embodiments, the cover member 20 can comprise any of a rigid material, such as stainless steel (e.g., 304 or grade 316L), titanium, an alloy of nickel and titanium (e.g., nitinol), and a synthetic fluoropolymer of tetrafluoroethylene such as polytetrafluoroethylene (PTFE). A thread 80 can be positioned between the support member 40 and the cover member 20. The thread 80 can extend along a longitudinal length of the support member 40. The cover member 20 can prevent contamination or damage to the thread 80.

In accordance with some embodiments, a physician can hold the insertion device 10 by the base 60, and the distal portion of the device directed through the skin 90 of a patient so that a portion of the device and thread are positioned under the skin 90. The physician can advance the support member 40 and the cover member 20 into the skin 90 of the patient by piercing the skin 90 using a sharp portion of the support member 40 and/or the cover member 20. In some methods, the skin 90 of the patient can be pierced or cut open before directing the insertion device 10 into the patient.

Once the skin 90 has been pierced and the support member 40 and the thread 80 are positioned subcutaneously, the cover member 20 can be removed from the device 10. For example, the cover member 20 can be removed from the distal portion of the insertion device 10 before or after engaging the insertion device 10 against the skin 90. In some embodiments, the insertion device 10 can be configured so that the cover member 20 is removed from the distal portion as the insertion device 10 is inserted into the skin 90. Further, in some embodiments, the insertion device 10 can also or alternatively be configured so that the cover member 20 is inserted into the skin 90 and then removed. For example, the insertion device 10 can be configured so that a portion of the device, e.g., the cover member 20, is inserted through a first portion of the skin 90 and removed through a second portion of the skin 90. Additionally, in some embodiments, the cover member 20 can be left in situ after implantation and be partially or fully dissolvable within the skin 90.

Referring now to FIGS. 2-5, some embodiments can be configured such that after the cover member of the device has been used to protect a HA thread during insertion, the cover member can be removed from the device. For example, FIGS. 2-5 illustrate an insertion device 150 that can comprise a removable cover member 152, a base 154, a support member 160, and a HA thread 80, as illustrated in FIGS. 2-5. The insertion device 150 can be inserted into a patient with the thread 80 positioned between the support member 160 and the cover member 152. The thread 80 can be exposed and/or released by separating the cover member 152 from the insertion device.

Figure 2:
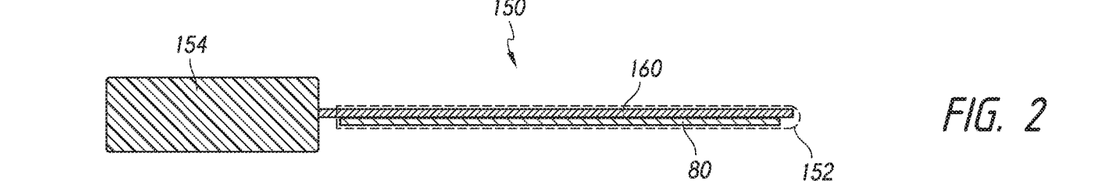
FIGS. 2-5 are cross-sectional side views of an insertion device and a method of inserting the device into a patient, according to some embodiments.

The support member 160 can be configured to maintain alignment of a thread relative to an insertion device and permit positioning of the thread within the patient. The support member 160 can comprise a proximal portion and a distal portion. As illustrated in FIG. 2, the proximal portion of the support member 160 can be coupled to the base 154, and the distal portion of the support member 160 extending from the base 154.

The distal portion of the support member 160 that extends from the base 154 can comprise a shaft having a longitudinal length. A cross-sectional profile through the longitudinal length of the support member 160 can be non-tubular. At the distal portion of the support member 160, distal to the base 154, the support member 160 comprises a blunt surface having an annular or radial profile. The blunt surface permits the insertion device 150 to be inserted into a patient without piercing or causing damage to the patient's tissue. The blunt surface can prevent damage to the cover member 152 that extends around the support member 160.

The cover member 152 extends around the distal portion of the support member 160. The cover member 152 can extend around the outer surface of the support member. The cover member 152 can comprise a proximal portion and a distal portion. The proximal portion of the cover member 152 can be coupled to the base 154. The distal portion of the cover member 152 can comprise a closed distal portion. An inner cavity can extend from the proximal portion of the cover member 152 toward the distal portion. A non-tubular support member can extend within the inner cavity of the cover member 152.

A thread 80 can be positioned between the support member 160 and the cover member 152. The thread can be engaged against an outer surface of the support member 160 and inner surface of the cover member 152. The thread 80 can be positioned so that a longitudinal length of the thread 80 extends along a longitudinal length of the support member 160.

The cover member 152 can urge the thread 80 against the support member 160 to maintain an orientation or position of the thread 80 relative to the insertion device 150. The cover member 152 can comprise a flexible material, e.g., a membrane, configured to conform to a shape of the support member 160 and/or thread 80. The cover member 152 can extend around the support member 160 and thread 80. The cover member 152 can be a material that is coated or applied to the support member 160 and/or thread 80.

The cover member 152 can prevent contamination of the thread 80 from exposure to an ambient environment, or from a person touching the thread 80. Damage to the thread can be avoided by preventing inadvertent touching or engagement of the thread 80. The cover member 152 and base 154 can prevent moisture from the patient's skin or tissue, e.g., dermis, epidermis, and/or subcutaneous tissue, from moving through or around the cover member to the thread 80. The cover member 152 can seal the inner cavity from ingress of fluid toward the thread 80 to avoid hydration of the thread 80 during insertion of the cover member 152 into the patient.

To use the insertion device 150, the thread 80 can be positioned between the support member 160 and the cover member 152, so that the cover member 152 encloses the thread 80. The insertion device 150 can be directed toward a patient. The distal portion of the cover member 152, having the support member 160 and thread 80 therein, can be moved through an opening in a first portion of the patient's skin 90.

Figure 3:
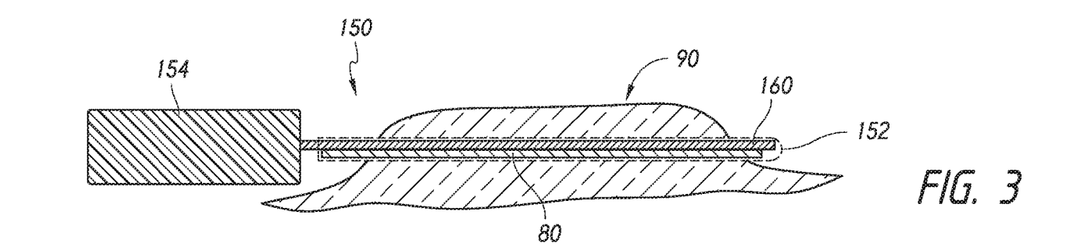

The insertion device 150 can be moved into the patient until a portion of the cover member 152 and support member 160 exit through a second portion of the patient's skin 90, as illustrated in FIG. 3. The insertion device 150 can be moved around a longitudinal and transverse axis of the device to position the thread 80 at a specific location. Movement of the insertion device 150 can comprise inserting, retracting, pitching, rolling, and/or yawing relative to the longitudinal and transverse axis and the patient.

Figure 4:
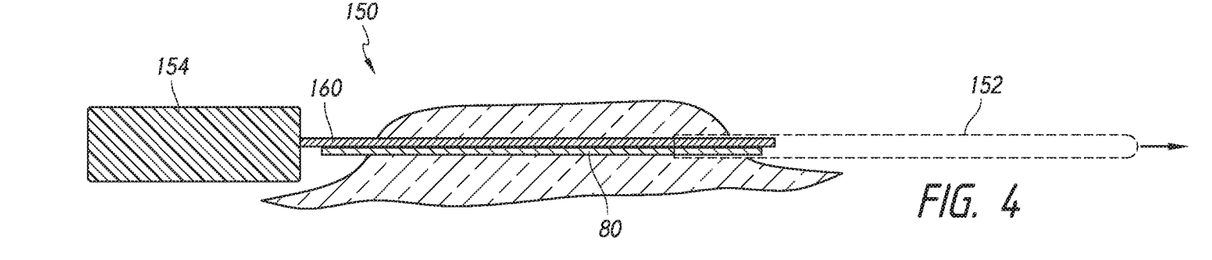

When the thread 80 is in a position where it is to be implanted, the cover member 152 can be separated from the base 154. The cover member 152 can be separated from the base 154 and withdrawn from the patient through the second portion of the patient's skin 90, as illustrated in FIG. 4. A proximal portion of the cover member 152 can be torn when the cover member 152 and is withdrawn from the patient. A release member of the base 154 can be actuated to permit separation of the cover member 152 from the base 154. When the cover member 152 is withdrawn, the support member 160 and the thread 80 are exposed to the patient.

Figure 5:
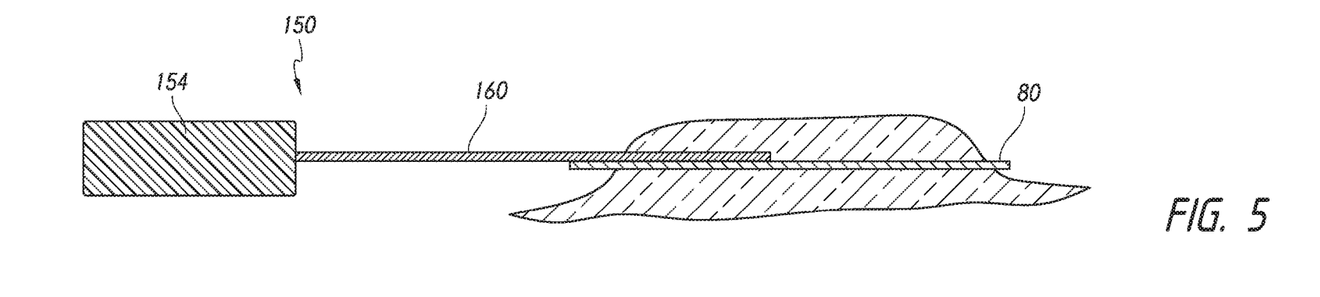

The support member 160 can be removed from the patient by retracting the base 154 to withdraw the support member 160 from the first portion of the patient's skin 90, as illustrated in FIG. 5. Any portion of the thread 80 that remains extending through the surface of the patient's skin can be separated or cut so that the remaining portion is entirely within the patient's skin.

The cover member can comprise a material configured to dissolve, degrade, or separate from the insertion device. The cover member can comprise a biologically safe and compatible material. The cover member can dissolve in response to a stimulus, for example, when exposed to a substance, material, and/or temperature. In some embodiments, the cover member remains solid when exposed to a first temperature, and dissolves when exposed a second temperature. The first temperature can comprise a range of temperatures typical of an ambient atmosphere outside of a human or animal body, while the second temperature can comprise a range of temperatures typically found within a human or animal body. The cover member can surround and enclose a thread and support member to prevent contamination or damage to the thread, and dissolve or separate from the thread after being exposed to condition that causes the cover member to dissolve.

Figure 6:
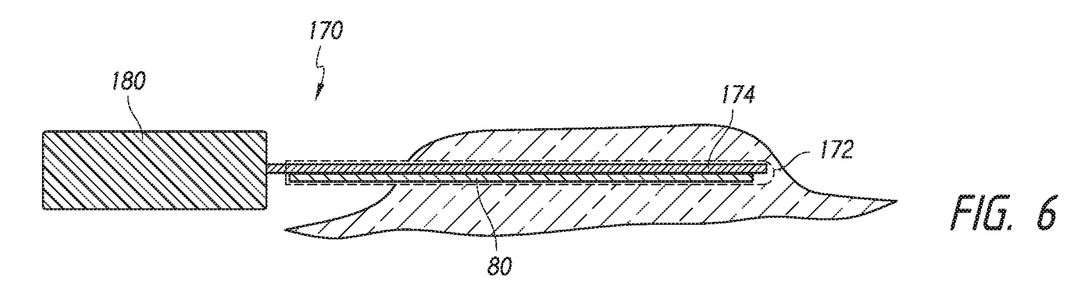
FIGS. 6-8 are cross-sectional side views of another insertion device and a method of inserting the device into a patient, according to some embodiments.
Figure 7:
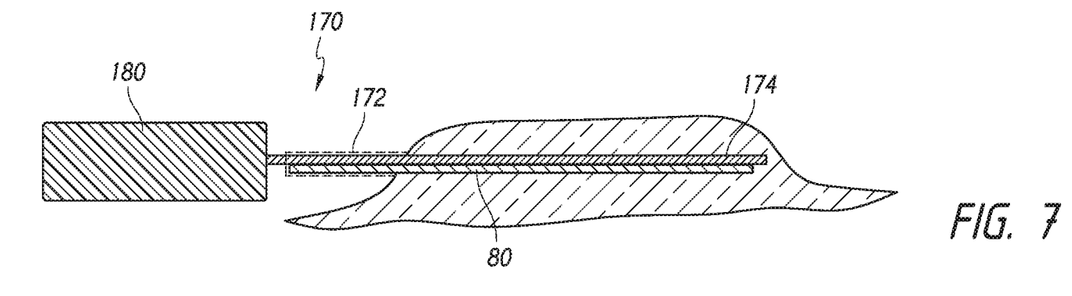
Figure 8:
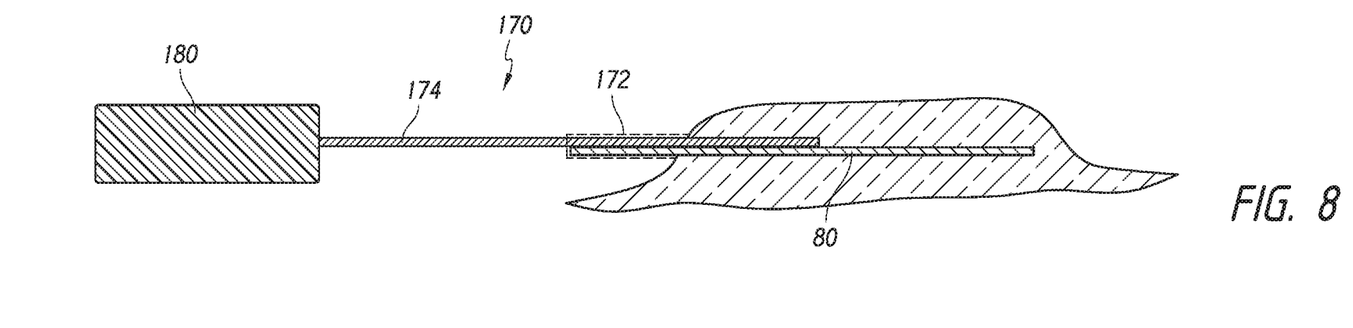

Referring now to FIGS. 6-8, some embodiments can be configured such that, after the cover member has used to protect the thread during insertion into the skin, the cover member of the device can dissolve over time in situ, thus obviating the need to remove the cover member from the skin. For example, the embodiment shown in FIGS. 6-8 illustrates an insertion device 170 comprising a dissolvable cover member 172 that extends around a support member 174 and a HA thread 80. The cover member 172 can be moved through an opening in the patient's skin 90, as illustrated in FIG. 6. After being inserted into the patient, the cover member 172 can dissolve in situ. A portion of the cover member 172, exposed to the ambient subcutaneous environment, can dissolve to expose the thread 80, as illustrated in FIG. 7. In some embodiments, a fluid can be directed through the insertion device 170 to the cover member 172 to cause the cover member 172 to dissolve.

The thread 80 can be separated from the support member 174 by retracting a base 180 of the device 170 to withdraw the support member 174 from the patient, as illustrated in FIG. 8. Any portion of the thread 80 that remains extending through the surface of the patient's skin can be separated or cut so that the remaining portion is entirely within the patient's skin.

Referring now to FIGS. 9-12, some embodiments of the insertion device can be configured to comprise multiple components that can move relative to each other to proximally retract the cover member relative to the support member in order to expose a HA thread. For example, FIGS. 9-12 illustrate an insertion device 200 that comprises a cover member 210 and a support member 212 that are movable relative to each other to expose a HA thread 80. A portion of the device 200 can be inserted into a patient, and the cover member 210 can be proximally retracted from around the support member 212 to expose the thread 80.

Figure 9:
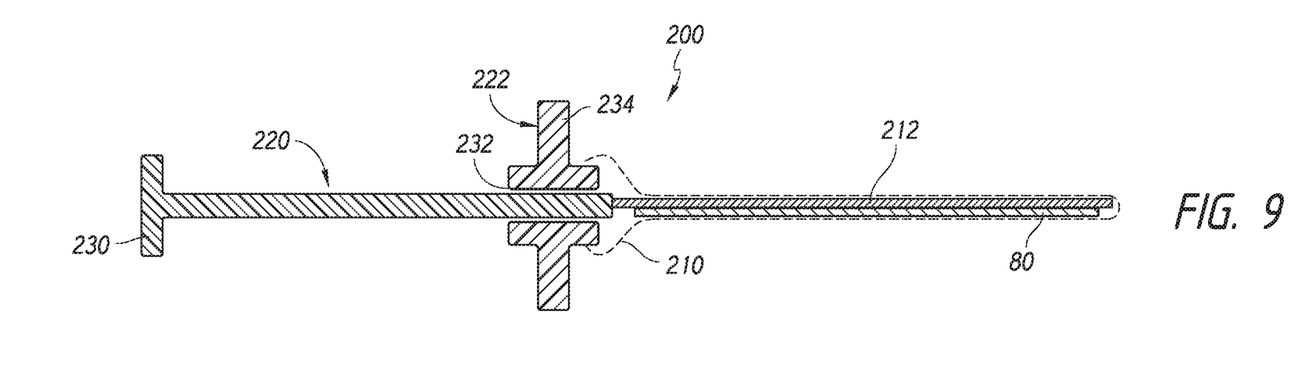
FIGS. 9-12 are cross-sectional side views of yet another insertion device and a method of inserting the device into a patient, according to some embodiments.

For example, in accordance with some embodiments, FIG. 9 illustrates that the support member 212 can be coupled to a first base 220, and the cover member 210 can be coupled to a second base 222. The first base 220 and the second base 222 can be movable relative to each other to expose the thread 80.

The first base 220 can comprise a proximal portion and a distal portion. The proximal portion of the first base 220 can comprise a handle 230 that extends from the first base 220. The handle 230 can extend transverse to a longitudinal length of the first base 220 so that a cross-sectional profile of the first base 220 is T-shaped. The handle 230 can comprise a flange, a disk, and/or a ring at the proximal portion of the first base 220. The handle can be configured to be engaged by a portion of the physician's hand, e.g., a palm or finger.

The support member 212 can extend from the distal portion of the first base 220. The support member 212 can maintain alignment of a thread relative to the insertion device 200 and permit positioning of the thread within the patient. The support member 212 can comprise a proximal portion and a distal portion. The proximal portion of the support member 212 can be coupled to the first base 220, and the distal portion of the support member 212 can extend from the first base 220. The support member 212 can have a longitudinal axis between the proximal and distal portions.

The second base 222 can comprise a proximal portion and a distal portion. A through-hole 232 can extend through the second base 222, between the proximal and distal portions. The through-hole 232 can comprise an inner surface having a profile that corresponds with a profile of the outer surface of the first base 220. The through-hole 232 can comprise a diameter that is approximately equal to or greater than the diameter of the outer surface of the first base 220.

The second base 222 can comprise a handle 234 that extends from an outer surface of the second base 222. The handle 234 can extend from between the proximal and distal portions of the second base 222. The handle 234 can extend transverse to a longitudinal axis of the second base 222. The handle 234 can comprise a flange, a disk, and a ring at the proximal portion of the first base 220. The handle can be configured to be engaged by a portion of the physician's hand, or one or more finger of the physician, e.g., the physician's index and middle fingers.

The cover member 210 can extend from the distal portion of the second base 222. The cover member 210 can comprise a proximal portion and a distal portion. The cover member 210 can have a longitudinal axis between the proximal and distal portions. A longitudinal length of the cover member 210 can be approximately equal to or greater than a longitudinal length of the support member 212. The cover member 210 can have a perimeter at a proximal portion that is coupled to the second base 222, and extends around the through-hole 232. A second portion of the cover member can be closed so that an inner cavity extends from the proximal portion of the second base 222 toward the distal portion of the cover member 210.

The insertion device 200 can be configured with a distal portion of the first base 220 positioned to extend through the through-hole 232 of the second base 222. The first base 220 can extending through the second base 222, and the support member 212 can extend within the cavity of the cover member 210.

In a first configuration, the second base 222 is positioned at a distal-most portion of the first base 220 so that a distal-most portion of the support member 212 is adjacent to the distal-most portion of the cover member 210. In the first configuration, illustrated in FIG. 9, the cover member 210 extends from the second base 222 around the outer side surfaces and the second and portion of the support member 212. Because the cover member 210 comprises a longitudinal length that is approximately equal to or longer than the longitudinal length of the support member 212, the support member remains within the inner cavity of the cover member 210 in the first configuration.

A thread 80 can be positioned between the support member 212 and the cover member 210. The thread can be engaged against an outer surface of the support member 212 and inner surface of the cover member 210. The thread 80 can be positioned so that a longitudinal length of the thread 80 extends along a longitudinal length of the support member 212.

Figure 11:
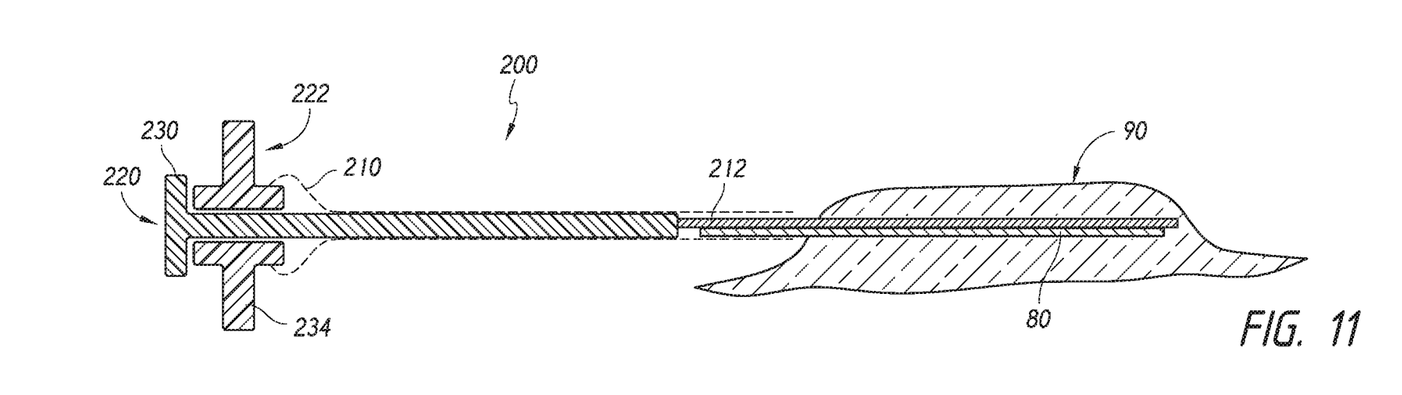

The first base 220 and/or the second base 222 can be moved relative to each other to actuate the insertion device 200. When the insertion device 200 is actuated, the first base 220 and the second base 222 can be moved to a second configuration, as illustrated in FIG. 11. In the second configuration, the second base 222 can be positioned at a proximal portion of the first base 220. The second base 222 can be retracted along the distal portion of the first base 220. The second base 222 can be moved along the first base 220 until the proximal portion of the second base 222 engages the handle 230.

When the insertion device is actuated, the cover member 210 can remain coupled to the second base 222. When the second base 222 is retracted along the distal portion of the first base 220, the inner surface of the distal-most portion of the cover member 210 can engage the distal-most portion of the support member 212. Movement of the second base 222 along the first base 220 can cause the support member 212 to separate or tear the cover member 210.

Figure 10:
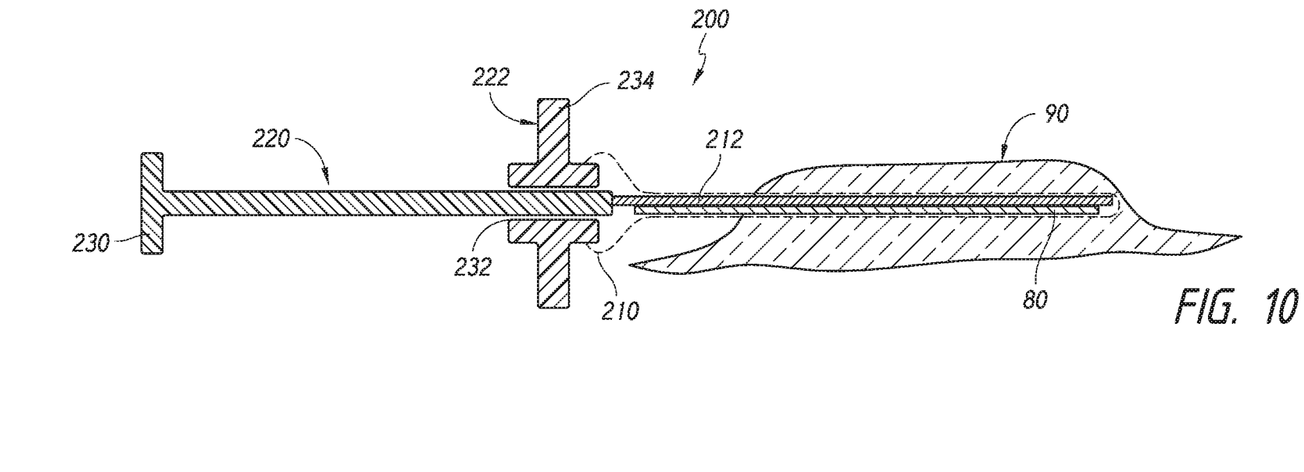

To use the insertion device 200, the thread 80 can be positioned between the support member 212 and the cover member 210 so that the cover member 210 encloses the thread 80. The insertion device 200 can be directed toward a patient in the first configuration. The distal portion of the cover member 210, having the support member 212 and thread 80 therein, can be moved through an opening in the patient's skin 90, as illustrated in FIG. 10. The insertion device 200 can be moved relative to a longitudinal and transverse axis of the device to position the thread 80 at a specific location. In some methods, movement of the insertion device 200 can comprise of inserting, retracting, pitching, rolling, and/or yawing relative to the longitudinal and transverse axis and the patient.

When the thread 80 is in the position where it is to be implanted, the insertion device 200 can be actuated to the second configuration. To actuate the insertion device 200, the physician can retract the second base 222 along the first base 220. The physician can move the second base 222 by using their fingers to pull the handle 234 of the second base toward the handle 230 of the first base. As the second base 222 and cover member 210 are moved, the support member 212 can cause the cover member 210 to separate or tear. The second base 222 can be retracted until the cover member 210 is withdrawn from the patient, as illustrated in FIG. 11. When the cover member 210 is withdrawn, the support member 212 and the thread 80 are exposed to the patient. A release member of the first or second base 220, 222 can be actuated to permit movement of the second base 222 relative to the first base 220.

Figure 12:
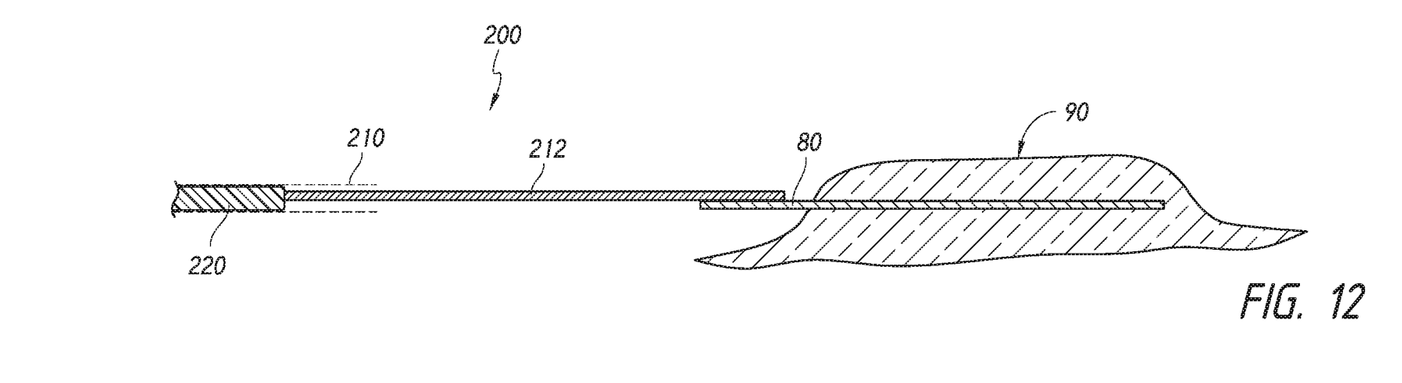

The support member 212 can be removed from the patient by retracting the first base 220 to withdraw the support member 212 from the patient's skin 90, as illustrated in FIG. 12. Any portion of the thread 80 that remains extending through the surface of the patient's skin can be separated or cut so that the remaining portion is entirely within the patient's skin.

FURTHER CONSIDERATIONS

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The subject technology is illustrated, for example, according to various aspects described below. Various examples of aspects of the subject technology are described as numbered clauses (1, 2, 3, etc) for convenience. These are provided as examples and do not limit the subject technology. It is noted that any of the dependent clauses may be combined in any combination, and placed into a respective independent clause, e.g., clause 1 or clause 5. The other clauses can be presented in a similar manner.

Clause 1. A thread insertion assembly comprising: a cover member comprising a proximal portion, a closed distal portion, and an inner cavity extending from the proximal portion toward the closed distal portion, a non-tubular support member extends within the inner cavity of the cover member, wherein the cover member is moveable relative to the support member to expose the thread; and a thread positioned along a longitudinal length of support member, between the support member and the cover member.

Clause 2. The thread insertion assembly of Clause 1, further comprising a first base, wherein the proximal portion of the cover member is coupled to the first base.

Clause 3. The thread insertion assembly of any one of the Clauses 1 to 2, comprising a first base, wherein the support member comprises a proximal portion coupled to the first base.

Clause 4. The thread insertion assembly of Clause 3, comprising a second base, wherein the proximal portion of the cover member is coupled to the second base.

Clause 5. The thread insertion assembly of Clause 4, wherein the cover member and second base are moveable relative to the first base and support member to expose the thread.

Clause 6. The thread insertion assembly of any one of the Clauses 4 to 5, wherein the second base comprises a through-hole, and wherein the first base extends through the through-hole of the second base.

Clause 7. The thread insertion assembly of any one of the Clauses 1 to 6, wherein the cover member comprises a biodegradable material configured to degrade within a patient to expose the thread.

Clause 8. The thread insertion assembly of any one of the Clauses 1 to 7, wherein the non-tubular support member comprises a flat cross-sectional profile.

Clause 9. The thread insertion assembly of any one of the Clauses 1 to 8, wherein the cover member comprises polytetrafluoroethylene ("PTFE").

Clause 10. The thread insertion assembly of any one of the Clauses 1 to 9, further comprising a base, the support member comprising a proximal end being coupled to the base, wherein the cover member comprises a biocompatible material and is removably positioned about the support member and the thread.

Clause 11. The thread insertion assembly of Clause 9, wherein the proximal portion of the cover member is coupled to the base, the cover member being configured to be separated from the base in a distal direction.

Clause 12. The thread insertion assembly of Clause 9, wherein the proximal portion of the cover member is coupled to a portion of the base, wherein the portion of the base is proximal retractable relative to the support member, and wherein the closed distal portion of the cover member is configured to open upon proximal retraction of the base relative to the support member to permit the support member and the thread to pass distally through the opened distal portion of the cover member.

Clause 13. The thread insertion assembly of any one of the Clauses 1 to 12, wherein the thread is retained against an outer surface of the support member by cover member.

Clause 14. The thread insertion assembly of any one of the Clauses 1 to 13, wherein at least a portion of the support member is less flexible relative to the cover member.

Clause 15. The thread insertion assembly of any one of the Clauses 1 to 14, wherein an outer surface of the support member defines a cross-sectional profile having a non-tubular or non-closed cross-section, which can conform to an outer surface of the thread.

Clause 16. A thread insertion assembly comprising: a moveable member comprising a proximal portion and a distal portion that extends along a portion of a thread, wherein the distal portion of the moveable member comprises laterally extending portions that surround a circumference of the thread in a first configuration, and circumferentially unfolds away from the thread in a second configuration to expose the thread.

Clause 17. The thread insertion assembly of Clause 16, wherein the distal portion of the moveable member extends along the distal portion of the thread.

Clause 18. The thread insertion assembly of Clause 17, wherein a longitudinal length of the moveable member, along the distal portion of the thread, remains constant in the first and second configurations.

Clause 19. The thread insertion assembly of any one of the Clauses 16 to 18, wherein the distal portion of the moveable member defines a cavity in the first configuration.

Clause 20. The thread insertion assembly of Clause 19, wherein the cavity comprises a closed distal portion enclosing the cavity.

Clause 21. The thread insertion assembly of any one of the Clauses 16 to 20, comprising a base coupled to the proximal portion of the moveable member.

Clause 22. The thread insertion assembly of any one of the Clauses 16 to 21, wherein the laterally extending portions expand in the second configuration.

Clause 23. A method of inserting a thread comprising: inserting a distal portion of a cover member into a patient, wherein the cover member comprises a proximal portion, a closed distal portion, and an inner cavity extending from the proximal portion toward the closed distal portion, and wherein a non-tubular support member extends within the inner cavity from the proximal portion toward the closed distal portion; and moving the cover member relative to the support member to expose a thread positioned along a longitudinal length of support member, between the support member and the cover member.

Clause 24. The method of Clause 23, comprising creating an opening through a patient's skin to permit insertion of the distal portion of the cover member.

Clause 25. The method of any one of the Clauses 19 to 20, wherein moving the cover member relative to the support member to expose the thread comprises retracting a second base, coupled to a proximal portion of the cover member, relative to a first base, coupled to a proximal portion of the support member.

Clause 26. The method of any one of the Clauses 23 to 25, wherein moving the cover member relative to the support member to expose the thread comprises retracting the distal portion of the cover member from the patient.

Clause 27. The method of any one of the Clauses 23 to 26, wherein moving the cover member relative to the support member to expose the thread comprises retracting a distal portion of the support member from the patient.

Clause 28. The method of any one of the Clauses 23 to 27, wherein moving the cover member relative to the support member to expose the thread comprises moving the cover member distal to the base.

Clause 29. The method of any one of the Clauses 23 to 28, wherein inserting a distal portion of a cover member into a patient comprises, inserting a distal portion of a cover member into a patient through at a first point, and moving the cover member relative to the base comprises moving the cover member to exit the patient at a second point, different than the first point.

Clause 30. The method of Clause 29, wherein moving the cover member relative to the support member to expose the thread comprises retracting the distal portion the support member from the first point of the patient.

Clause 31. The method of any one of the Clauses 23 to 30, wherein moving the cover member relative to the support member to expose the thread comprises permitting the cover member to remain within the patient.

Clause 32. A method of inserting a thread comprising: inserting a distal portion of a moveable member into a patient, in a first configuration, wherein the moveable member extends along distal portion of a thread and surrounds a circumference of the thread; and unfolding the moveable member away from the thread in a second configuration to expose the thread.

Clause 33. The method of Clause 32, comprising retracting the distal portion of the moveable member from the patient.

Clause 34. The method of Clause 33, comprising retracting the moveable member in the first configuration.

Clause 35. The method of any one of the Clauses 33 to 34, comprising retracting the moveable member in the second configuration.

Clause 36. The method of any one of the Clauses 32 to 35, wherein unfolding the moveable member comprises exposing the moveable member to a temperature of at least 85 degrees Fahrenheit.

Clause 37. The method of any one of the Clauses 32 to 36, wherein unfolding the moveable member comprises exposing the moveable member to a temperature of at least 90 degrees Fahrenheit.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more," Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

What is claimed is:

1. A thread insertion assembly comprising:
   a base,
   a flexible cover member comprising a proximal portion, a closed distal portion, and an inner cavity extending from the proximal portion of the cover member toward the closed distal portion of the cover member,
   a non-tubular support member comprising a proximal portion coupled to the base, the support member extends within the inner cavity of the cover member, and
   a thread positioned along a longitudinal length of support member, between the support member and the cover member,
   wherein the flexible cover member conforms to a shape of the support member and is separable from and distally slideable relative to the thread in situ, and wherein the support member is separable from and proximally slideable relative to the thread in situ to separate the thread from the support member and expose the thread.

2. The thread insertion assembly of claim 1, wherein the proximal portion of the cover member is coupled to the base.

3. The thread insertion assembly of claim 1, wherein the non-tubular support member comprises a flat cross-sectional profile.

4. The thread insertion assembly of claim 1, wherein the cover member comprises a biodegradable material configured to degrade within a patient to expose the thread.

5. The thread insertion assembly of claim 1, wherein the cover member comprises a biocompatible material and is removably positioned about the support member and the thread.

6. The thread insertion assembly of claim 5, wherein the proximal portion of the cover member is coupled to the base, the cover member being configured to be separated from the base in a distal direction.

7. The thread insertion assembly of claim 1, wherein the thread is a dermal filler thread.

8. The thread insertion assembly of claim 1, wherein the thread comprises hyaluronic acid.

9. A method of inserting a thread comprising:
   inserting a distal portion of a flexible cover member into a patient, wherein the cover member comprises a proximal portion, a closed distal portion, and an inner cavity extending from the proximal portion of the cover member toward the closed distal portion of the cover member, wherein a non-tubular support member, comprising a proximal portion coupled to a first base, extends within the inner cavity from the proximal portion of the cover member toward the closed distal portion of the cover member, and wherein the flexible cover member conforms to a shape of the support member; and
   distally sliding the cover member relative to the thread, in situ, to separate the cover member and expose a thread positioned along a longitudinal length of support member, between the support member and the cover member.

10. The method of claim 9, comprising creating an opening through a patient's skin to permit insertion of the distal portion of the cover member.

11. The method of claim 9, wherein separating the cover member relative to the thread to expose the thread comprises withdrawing the distal portion of the cover member from the patient.

12. The method of claim 9, wherein separating the cover member relative to the thread to expose the thread comprises proximally sliding the support member from the patient.

13. The method of claim 9, wherein separating the cover member relative to the thread to expose the thread comprises distally sliding the cover member relative to the base.

14. The method of claim 9, wherein inserting a distal portion of a cover member into a patient comprises, inserting a distal portion of a cover member into a patient through at a first point, and separating the cover member relative to the base comprises moving the cover member to exit the patient at a second point, different than the first point.

15. The method of claim 14, wherein separating the cover member relative to the thread to expose the thread comprises retracting the distal portion the support member from the first point of the patient.

16. The method of claim 9, wherein separating the cover member relative to the support member to expose the thread comprises permitting the cover member to remain within the patient.

17. A thread insertion assembly comprising:
a flexible cover member comprising a proximal portion, a closed distal portion, and an inner cavity extending from the proximal portion of the cover member toward the closed distal portion of the cover member,
a non-tubular support member extends within the inner cavity of the cover member, the support member comprising any of a shaft, rod, or plate, wherein the flexible cover member conforms to a shape of the support member and is separable from and distally slideable relative to the thread in situ, and
a thread positioned along a longitudinal length of support member, between the support member and the cover member, wherein the support member is separable from the thread in situ to expose the thread.

18. The thread insertion assembly of claim 17, further comprising a base, wherein a proximal portion of the non-tubular support member is coupled to the base.

19. The thread insertion assembly of claim 17, further comprising a base, wherein the proximal portion of the cover member is coupled to the base.

20. The thread insertion assembly of claim 17, wherein the non-tubular support member comprises a flat cross-sectional profile.

21. The thread insertion assembly of claim 17, wherein the cover member comprises a biodegradable material configured to degrade within a patient to expose the thread.

22. The thread insertion assembly of claim 17, wherein the cover member comprises a biocompatible material and is removably positioned about the support member and the thread.

* * * * *